US009407796B2

(12) United States Patent
Dinten et al.

(10) Patent No.: US 9,407,796 B2
(45) Date of Patent: Aug. 2, 2016

(54) SYSTEM FOR RECONSTRUCTING OPTICAL PROPERTIES IN A DIFFUSING MEDIUM, COMPRISING A PULSED RADIATION SOURCE AND AT LEAST TWO DETECTORS OF TWO DIFFERENT TYPES, AND ASSOCIATED RECONSTRUCTION METHOD

(71) Applicant: Commissariat à l'énergie atomique et aux énergies alternatives, Paris (FR)

(72) Inventors: Jean-Marc Dinten, Lyons (FR); Jérôme Boutet, Claix (FR)

(73) Assignee: Commissariat á l'énergie atomique et aux énergies alternatives, Paris (FR)

( * ) Notice: Subject to any disclaimer, the term of this patent is extended or adjusted under 35 U.S.C. 154(b) by 642 days.

(21) Appl. No.: 13/723,625

(22) Filed: Dec. 21, 2012

(65) Prior Publication Data
US 2013/0162793 A1    Jun. 27, 2013

(30) Foreign Application Priority Data

Dec. 23, 2011    (FR) ...................................... 11 62412

(51) Int. Cl.
*H04N 9/47* (2006.01)
*H04N 5/222* (2006.01)
(Continued)

(52) U.S. Cl.
CPC ........... *H04N 5/222* (2013.01); *G01N 21/4795* (2013.01); *G01N 21/6408* (2013.01); *G01N 21/6456* (2013.01)

(58) Field of Classification Search
USPC ........................................................ 348/77
See application file for complete search history.

(56) References Cited

U.S. PATENT DOCUMENTS 4,637,719 A * 1/1987 Herman ........................... 356/72
4,843,619 A * 6/1989 Sheridan ....................... 378/207
(Continued)

FOREIGN PATENT DOCUMENTS

EP    2182343    5/2010
EP    2302362    3/2011
(Continued)

OTHER PUBLICATIONS

Steinvall, et al., High Resolution Ladar Using Time-Correlated Single Photon Counting, Proc. of SPIE, vol. 6950 (2008) (13 pages).
(Continued)

*Primary Examiner* — Leron Beck
(74) *Attorney, Agent, or Firm* — McCarter & English, LLP

(57) ABSTRACT

A system for reconstructing optical properties of a diffusing medium including at least one pulsed radiation source capable of illuminating the diffusing medium, at least one first detector of a first type, capable of receiving a signal emitted by the medium, the first detector being a time-resolved detector, and an information processing unit for processing at least one source—first detector pair, a time distribution of the signal received by the corresponding first detector. The reconstruction system also includes at least one second detector of a second type, each second detector being made up of a set of pixel(s) from an image sensor capable of acquiring an image of the medium, and the second detector being capable of measuring an intensity of the signal emitted by the medium, the intensity corresponding to an equivalent moment of order 0 for the corresponding source—second detector pair.

15 Claims, 3 Drawing Sheets

(51) Int. Cl.
  *G01N 21/47* (2006.01)
  *G01N 21/64* (2006.01)

(56) References Cited

U.S. PATENT DOCUMENTS

| | | | | |
|---|---|---|---|---|
| 6,108,576 | A * | 8/2000 | Alfano et al. | 600/476 |
| 6,498,863 | B1 * | 12/2002 | Gaidoukevitch et al. | 382/173 |
| 6,549,646 | B1 * | 4/2003 | Yeh et al. | 382/132 |
| 8,072,595 | B1 * | 12/2011 | Bastiaans et al. | 356/301 |
| 2004/0052430 | A1 * | 3/2004 | Albertelli et al. | 382/289 |
| 2004/0190134 | A1 * | 9/2004 | Tahara et al. | 359/386 |
| 2008/0037398 | A1 * | 2/2008 | Verschuren et al. | 369/112.01 |
| 2008/0067420 | A1 * | 3/2008 | Laidevant et al. | 250/459.1 |
| 2008/0260647 | A1 * | 10/2008 | Intes et al. | 424/9.6 |
| 2009/0047300 | A1 * | 2/2009 | Abulrob et al. | 424/185.1 |
| 2009/0266999 | A1 | 10/2009 | Krattiger | |
| 2011/0304724 | A1 * | 12/2011 | Yamazaki et al. | 348/80 |
| 2013/0126755 | A1 * | 5/2013 | Kemnitz | 250/459.1 |

FOREIGN PATENT DOCUMENTS

| WO | WO 2005/043138 | 5/2005 |
|---|---|---|
| WO | WO 2009/046985 | 4/2009 |

OTHER PUBLICATIONS

Search Report mailed on Aug. 6, 2012, issued in connection with French Patent Appln. No. 1162412 (3 pages).

* cited by examiner

SYSTEM FOR RECONSTRUCTING OPTICAL PROPERTIES IN A DIFFUSING MEDIUM, COMPRISING A PULSED RADIATION SOURCE AND AT LEAST TWO DETECTORS OF TWO DIFFERENT TYPES, AND ASSOCIATED RECONSTRUCTION METHOD

RELATED APPLICATIONS

This application claims the benefit of French Patent Application No. 1162412 filed on Dec. 23, 2011. The entire disclosure of this application is incorporated herein by reference.

FIELD OF THE INVENTION

The present invention relates to a system for reconstructing optical properties of a diffusing medium, the reconstruction system comprising:
- at least one pulsed radiation source capable of illuminating the diffusing medium,
- at least one first detector of a first type, capable of receiving a signal emitted by the medium, the or each first detector being a time-resolved detector,
- means for processing, for at least one source—first detector pair, a time distribution of the signal received by the corresponding first detector.

The invention also relates to a method for reconstructing the optical properties of a diffusing medium using such a reconstruction system.

The invention in particular relates to the field of optical diffusion imaging, for example fluorescence imaging on biological tissues, or the imaging of endogenous properties of those tissues (absorption, diffusion), and in particular optical molecular imaging on animals and optical molecular imaging on a human organ, such as the brain, a breast, the digestive tract, or other organs in which fluorophores may be injected.

The invention applies to the detection of breast cancer, prostate cancer, or digestive tract cancer, in particular the detection of pathologies on the surface of the digestive tract. The invention also applies to dermatology, in particular the characterization of a skin inflammation reaction.

BACKGROUND OF THE INVENTION

A reconstruction system of the aforementioned type is known from document EP 2 302 362 A1. It comprises a plurality of pulsed radiation sources to illuminate the medium of which one wishes to acquire an image, then process it, and a plurality of detectors receiving the signals emitted by the illuminated medium. Each pulsed source is a pulsed laser source or an optical fiber connected to an offboard pulsed laser.

Each detector is a time-resolved detector, i.e. a detector making it possible to measure the time distribution of the arrival time of the photons, also called TCPSC (Time-Correlated Single Photon Counting). According to a first embodiment, each detector includes a photomultiplier tube connected to an optical fiber transmitting the signal from the studied medium to the detector. According to a second embodiment, each detector includes a set of pixels of an intensified camera with a time gate, also called ultra-fast intensified gated camera.

The reconstruction system comprises means for producing, for each source-detector pair, a time distribution of the signal received by the detector, and a device for determining, as a function of the moments of order 0 and order 1 of the time distribution for each source-detector pair, the localization of the fluorophores(s) arranged in the medium.

However, the detectors of such a reconstruction system have a time and/or amplitude instability, which creates uncertainties affecting the time distribution. The determination of the optical properties of a diffusing medium require considering transforms of such distributions, in particular Mellin transforms, these transforms making it possible for example to establish moments of order 0 or order 1 used during the reconstruction process. It is then understood that these instabilities can affect the precision of the reconstruction.

The aim of the invention is therefore to propose a reconstruction system for the optical properties of a diffusing medium, making it possible to reduce the influence of parasitic fluctuations of the time distributions obtained by the time-resolved optical detectors, so as to improve the reconstruction of the optical properties.

SUMMARY OF THE INVENTION

To that end, the invention relates to a reconstruction system of the aforementioned type, wherein the system also comprises at least one second detector of a second type distinct from the first type, the or each second detector being made up of a set of pixel(s) from an image sensor capable of acquiring an image of the medium, in that the or each second detector is capable of measuring an intensity of the signal emitted by the medium, said intensity corresponding to an equivalent moment of order 0 for the corresponding source—second detector pair, and wherein the system also comprises means for computing at least one base parameter by combining a magnitude that is characteristic of the time distribution corresponding to at least one source—first detector pair with the intensity measured for at least one source—second detector pair, the optical properties being reconstructed from the computed base parameter.

According to other advantageous features of the invention, the reconstruction system comprises one or more of the following features, considered alone or according to all technically possible combinations:
- the or each second detector is a non-time-resolved detector,
- the system comprises means for computing the moment of order 0 of the time distribution for each source—first detector pair and the equivalent moment of order 0 for each source—second detector pair,
- the system comprises means for computing a single moment of order 1 of the time distribution for each source—first distribution pair,
- the system comprises a device for determining, as a function of the computed moments of order 0 and order 1, the localization of N fluorophore(s) in the medium, N being an integer greater than or equal to 1, each first detector being capable of receiving a fluorescence signal emitted by the fluorophore and each second detector being capable of measuring the intensity of the emitted fluorescence signal,
- the determination device includes means for producing a mesh of a volume of the medium, the mesh including M elementary link(s), M being an integer greater than or equal to 1, and means for distributing N fluorophore(s) in the medium, each fluorophore being distributed in one of the M link(s) of the medium according to a configuration, and means for computing at least one base parameter, the or each base parameter combining, for at least one time distribution, at least one magnitude obtained from at least one moment of said distribution and at least one estimate of that magnitude, the system also comprises a lens for focusing the signals emitted by the medium, each second detector being positioned in the image plane of the lens, the system also comprises an optical filter arranged between the medium and the image sensor, so as to filter the signals emitted by the medium to the image sensor, each first detector includes an optical fiber coupled to a time-resolved detection module, the image sensor is a CCD sensor or a CMOS sensor, the optical properties comprise at least one element from among the following group:

light absorption properties, characterized in particular by the absorption coefficient, diffusion properties, characterized in particular by the reduced diffusion coefficient or the diffusion coefficient, and fluorescence properties, in particular characterized by a response function of a fluorophore, or by a concentration of the fluorophore, or by a magnitude depending on a quantity of the fluorophore, the system comprises means for computing a correction factor associated with the time distribution of at least one source—first detector pair, the correction factor depending on the intensity measured by a second corresponding detector and the moment of order 0 computed for said at least one source—first detector pair.

The invention also relates to a method for reconstructing optical properties of a diffusing medium, using a reconstruction system including at least one pulsed radiation source, at least one first detector of a first type, the or each first detector being a time-resolved detector, the method comprising the following steps:

lighting the medium using the or each pulsed radiation source, reception, by the or each first detector, of a signal emitted by the medium, and processing, for at least one source—first detector pair, a time distribution of the signal received by the corresponding first detector, characterized in that it also comprises the following step:

measuring the intensity of the signal emitted by the medium by acquiring an image of the medium using at least one second detector of a second type distinct from the first type, said intensity corresponding to an equivalent moment of order 0 for the corresponding source—second detector pair, the or each second detector being included in the reconstruction system and made up of a set of pixel(s) from an image sensor.

According to another advantageous feature of the invention, the reconstruction method also comprises computing the moment of order 0 of the time distribution for each source—first detector pair and the equivalent moment of order 0 for each source—second detector pair.

BRIEF DESCRIPTION OF THE DRAWINGS

These features and advantages of the invention will appear upon reading the following description, provided solely as an example, and done in reference to the appended drawings, in which.

DETAILED DESCRIPTION OF PREFERRED EMBODIMENTS

Figure 1:
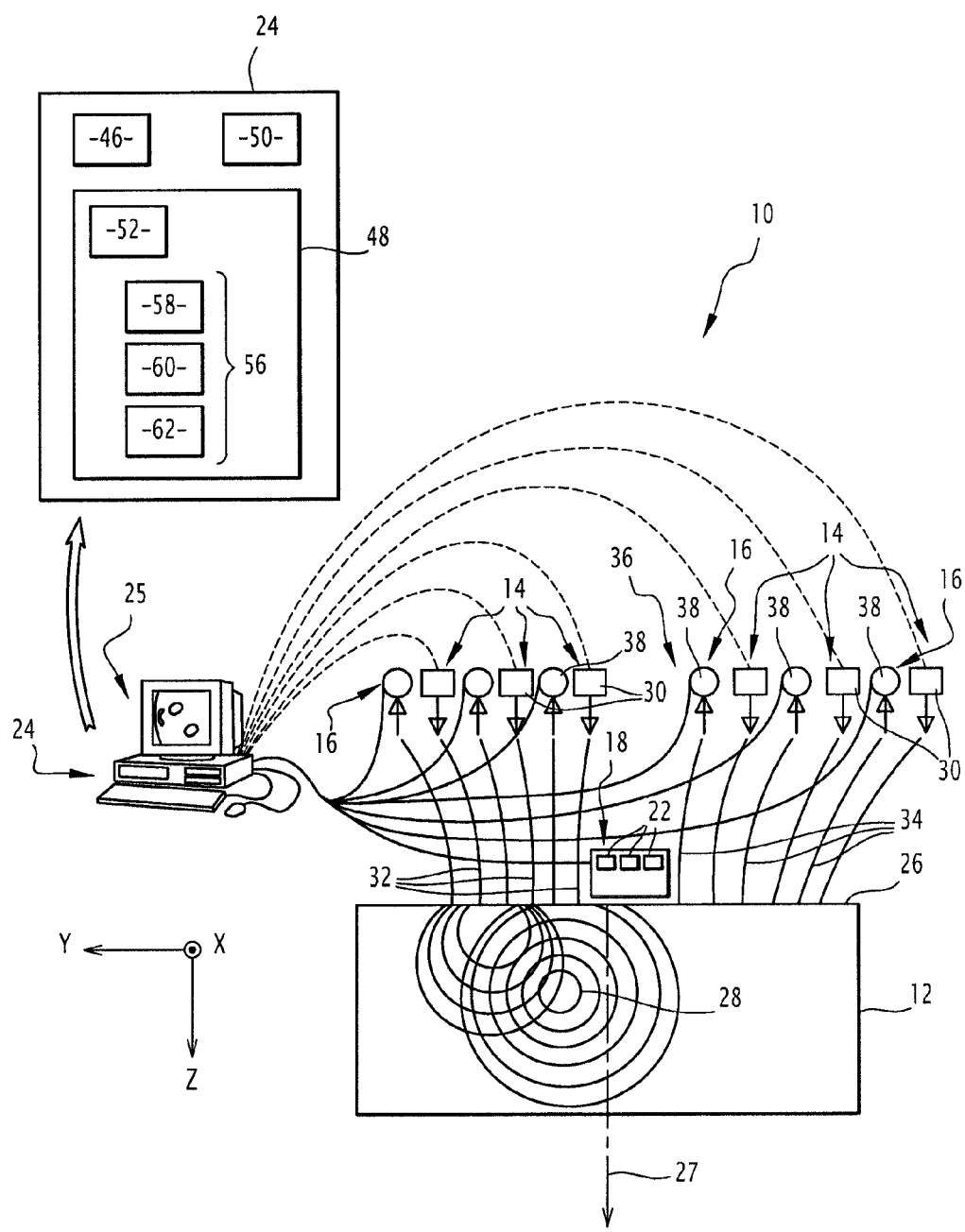
FIG. 1 is a diagrammatic illustration of a reconstruction system according to the invention, comprising an imaging probe including pulsed radiation sources and first and second detectors.

In FIG. 1, a reconstruction system 10 is designed to examine a diffusing medium 12, such as a biological tissue, by acquiring optical signals emitted by the medium 12 under the effect of an excitation radiation, then processing the signals to reconstruct the optical properties of that medium.

"Reconstruction of optical properties" for example refers to:

the reconstruction of the absorption properties, those properties in particular being characterized by the absorption coefficient, denoted $\mu_a$, or the reconstruction of the diffusion properties, those properties in particular being characterized by the reduced diffusion coefficient μ's or by the diffusion coefficient D', or the reconstruction of the fluorescence properties, those properties in particular being characterized by a response function F of a fluorophore, or by a concentration c of a fluorophore, or by any other magnitude expressing a quantity q of a fluorophore, said fluorophore for example being endogenous or exogenous.

The reconstruction system 10 comprises a plurality of pulsed radiation sources 14 capable of lighting the medium 12, a plurality of first detectors 16 of a first type, capable of receiving a signal emitted by the medium 12, and an image sensor 18 capable of acquiring an image of the medium 12. The radiation sources 14, the first detector 16 and the image sensor 18 are arranged in a probe 20, shown in FIGS. 2 and 3.

The reconstruction system 10 comprises a plurality of second detectors 22 of a second type distinct from the first type, and each second detector 22 is formed by a pixel or a set of pixels from the image sensor 18.

The system 10 comprises an information processing unit 24 and a monitor 25 for displaying an image of the medium 12.

Complementarily, the system 10 optionally comprises a white light source, not shown, to provide a base-light for the medium 12.

The medium 12 has an observation surface 26, in the form of a plane parallel to a longitudinal axis X and a transverse axis Y, and in contact with which the probe 20 can be applied. The medium 12 has an observation direction 27 extending along the vertical axis Z and substantially perpendicular to the observation surface 26. The depth of the medium 12 is measured from the observation surface 26 and in the direction of the observation direction 27.

The medium 12 includes biological tissues from an animal or a human. The medium 12 is for example an area of an organ such as the brain, a breast, the prostate, the digestive tract, or other organs in which fluorophores can be injected.

In the example embodiment of FIG. 1, the medium 12 is a diffusing medium containing fluorescent inclusions 28, also called for fluorophores. A single fluorophore 28 is shown in FIG. 1 for clarity of the drawing.

Each radiation source 14 includes a pulsed light source 30, also shown by an index s, and an excitation optical fiber 32 connected to the pulsed source 30 to transmit the light pulse to the medium 12.

In an alternative not shown, each radiation source 14 includes an excitation optical fiber 32 to connect to a single pulsed light source shared by the plurality of radiation sources 14. According to this alternative, the system 10 also comprises an optical switch or a multiplexer for selecting the excitation fiber 32 in which the light beam is sent. This is then called a fibrous source.

In general, when the light source is coupled to the excitation optical fiber 32, the end of the excitation optical fiber is assimilated to the source s.

Also alternatively, the set of radiation sources 14 is made up of a single pulsed light source and a mirror device of the MEMS (MicroElectroMechanical Systems) type, not shown, to sweep the medium 12 with the light coming from the pulsed light source.

The wavelength of each radiation source 14 is preferably in the red or near infrared range, i.e. comprised between 500 nm and 1300 nm. The repetition rate of the pulses from the source is approximately 50 MHz.

The pulses emitted by each radiation source 14 have a duration comprised between 500 picoseconds and 50 femtoseconds, each pulsed light source 30 being capable of generating a pulse with a duration lasting between 500 picoseconds and 50 femtoseconds.

Each first detector 16 is a time-resolved detector. Each first detector 16 includes a detection optical fiber 34 connected to a time-resolved detection module 36. "Time-resolved detector" refers to a detector capable of establishing a time distribution of the optical diffusion signal emitted by the medium in response to a pulsed light excitation.

In general, when the detector is coupled to a detection optical fiber 34, the end of the detection optical fiber is assimilated to the source d.

In the example embodiment of FIG. 1, the detection module 36 includes a detection member 38 for each first detector 16. In an alternative not shown, the detection module 36 includes a detection member shared by several first detectors 16, in particular a single detection member for all of the first detectors 16.

The first type of first detector 16 depends in particular on the detection member 38, the detection member 38 for example being a photomultiplier, or an avalanche photodiode (APD), or a single-photon avalanche diode (SPAD), or an image intensifier tube with one or more micro-channel plates.

The sensor 18 is a two-dimensional image sensor, i.e. in a plane parallel to the X and Y axes.

The sensor 18 is preferably a pixelated image sensor, such as a CCD (Charge-Coupled Device). Alternatively, the sensor 18 is a CMOS (Complementary Metal-Oxide Semiconductor) sensor.

Figure 2:
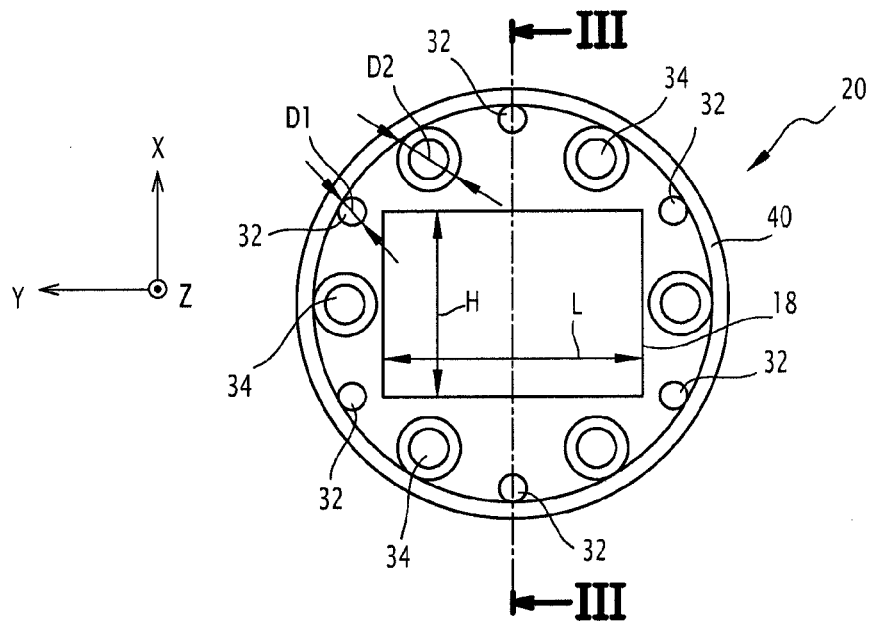
FIG. 2 is a front view of the probe of FIG. 1.

The image sensor 18 has a high-definition resolution, i.e. with a minimum of 720 pixels high, along the X axis in FIG. 2. The image sensor 18 has a height H along the X-axis of approximately 1.5 mm and a width L along the Y-axis of approximately 2 mm.

Figure 3:
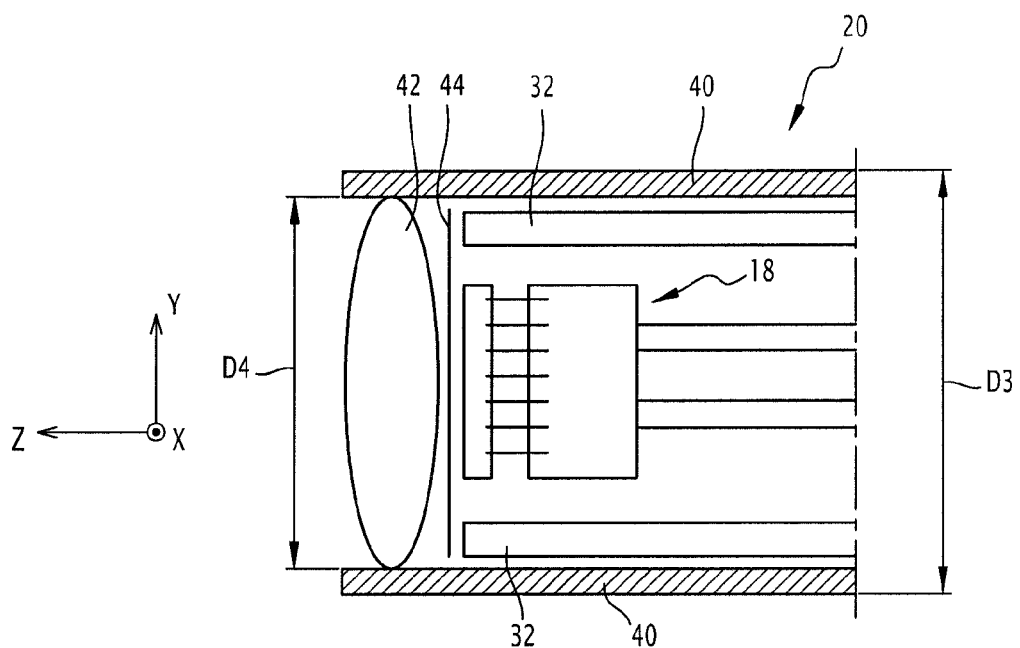
FIG. 3 is a cross-section in plane III of FIG. 2.
Figure 4:
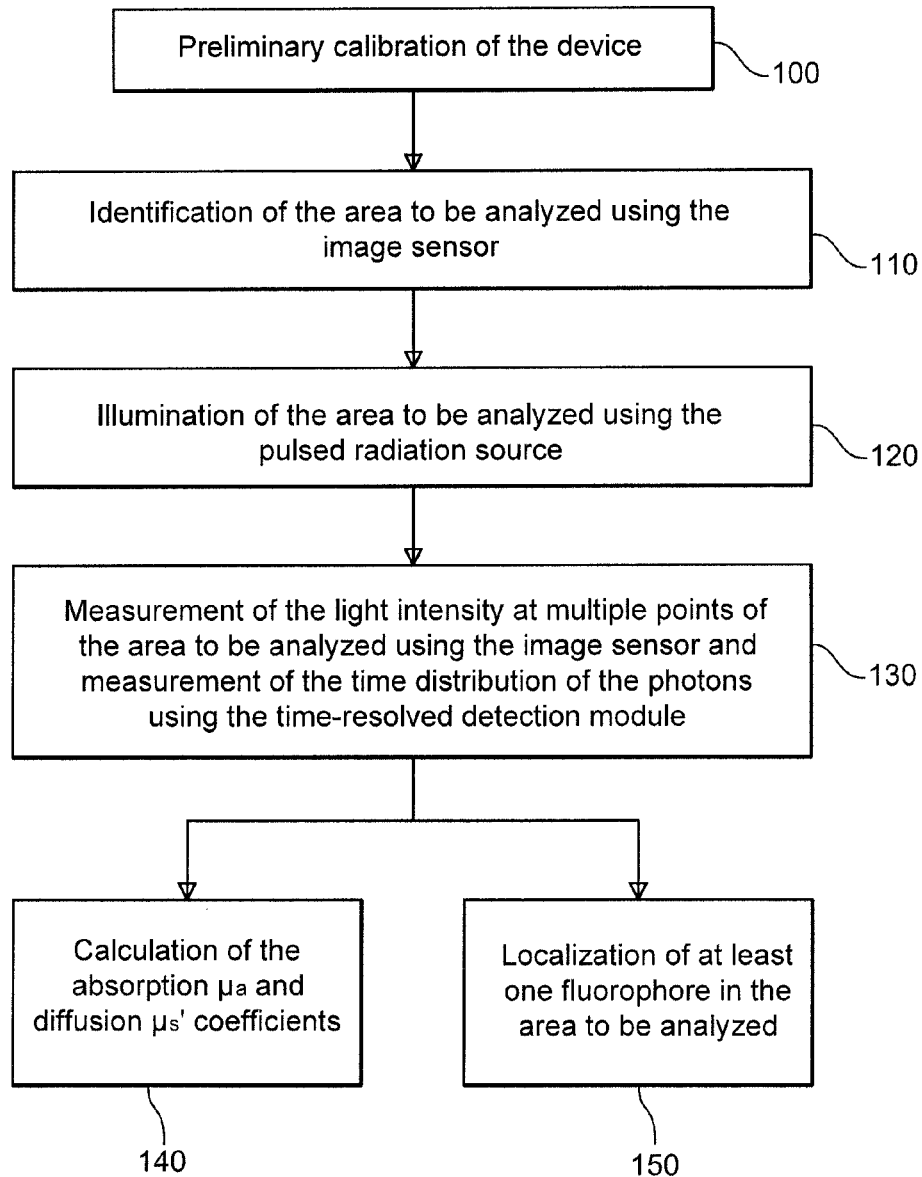
FIG. 4 is a flowchart of a reconstruction method according to the invention.

The probe 20 includes a protective housing 40 in which the excitation 32 and detection 34 fibers and the image sensor 18 are arranged, as shown in FIGS. 2 and 3. In the example embodiment of FIG. 2, the image sensor 18 is positioned substantially at the center of the optical fibers 32, 34, and the excitation 32 and detection 34 fibers are arranged alternating and circularly on the periphery of the image sensor 18.

The probe 20 includes a lens 42 for focusing signals emitted by the medium, as shown in FIG. 3. Each second detector 22 is positioned in the image plane of the lines 42. Each second detector 16 is also capable of being positioned in the image plane of the lines 42.

Complementarily, in the case of fluorescence imaging, the probe 20 comprises an optical filter 44 arranged in the medium 12 and the image sensor 18, so as to filter the signals emitted by the medium 12 to the first detectors 16 and second detectors 22. In the example embodiment of FIG. 3, the optical filter 44 is placed between the focusing lens 42 and the image sensor 18. The purpose of this filter is to eliminate the optical signals whereof the wavelength is different from a wavelength of interest. When one wishes to reconstruct the distribution of the fluorophores in a medium, this wavelength of interest is the fluorescence wavelength. When one wishes to reconstruct the optical diffusion or absorption properties of the medium, the wavelength of interest is the excitation wavelength of the source.

The source 20 is a compact probe for diagnosing certain cancers, such as a portable probe for diagnosing breast cancer, an endorectal probe for diagnosing prostate cancer, or a dermatological probe.

Alternatively, the probe 20 is an endoscopic probe, such as a flexible probe for diagnosing digestive cancer, the reconstruction system 10 being particularly suited for the detection of pathologies on the surface of the digestive tract.

Each second detector 22 can measure an intensity $I_{sd'}$ of the signal emitted by the medium 12 when the medium is lit by a light source 14, s and d' respectively representing an index of the source 14 and an index of the second detector 22. The measured intensity $I_{sd'}$ is a function of the gray level of the point(s) of the image acquired by the sensor 18 associated with the pixel(s) of the sensor forming the corresponding second detector 22, the index sd' designating the source—second detector pair used.

The second type of the second detector 22 is distinct from the first type of the first detector 16, each second detector 22 being made up of a set of pixels from the image sensor 18, whereas in the described embodiment, each first detector 16 includes a detection optical fiber 34 connected to a time-resolved detection module 36.

In the described embodiment, each second detector 22 is a non-time-resolved detector.

The information processing unit 24, shown in FIG. 1, includes a data processor 46 and a memory 48 associated with the processor 46.

The processing unit 24 includes means 50 for processing, for at least one source 14—first detector 16 pair, a time distribution denoted $M_{sd}(t)$ for the signal received by the corresponding first detector 16, s and d respectively representing the index of the source 14 and an index of the first detector 16. The processing means 50 are preferably made in the form of one or more electronic boards connected to the first detectors 14 and making it possible to measure the time-correlated single photon counting (TCPSC).

Each pulsed light source 30 includes a pulsed laser. Alternatively, each pulsed light source 30 includes a laser diode. Also alternatively, each pulsed light source 30 includes a constant light source whereof the light intensity is modulated in pulses of equivalent duration by a quick-closing device. The quick-closing devices is a piezoelectric actuator, an acousto-optical crystal, a Pockels cell, or a collector optical cell.

In the example embodiment of FIGS. 1 and 3, the optical axis of each excitation optical fiber 32 extends, near the end of the fiber, along the Z axis and perpendicular to the observation surface 26. The ends of the excitation fibers 32 are distributed along a plane perpendicular to the Z axis and parallel to the observation surface 26. In one alternative not shown, the optical axis of each excitation optical fiber 32 extends, in the vicinity of the end of the fiber, obliquely relative to the Z axis, so as to emit light at an angle relative to the observation surface 26, while preferably intercepting the field of the image sensor 18. Each excitation optical fiber 32 has a first diameter D1, with a substantially constant value from one fiber 32 to the next, as shown in FIG. 2. The value of the first diameter D1 is preferably equal to 65 μm, and typically comprised between 10 μm and 1 mm.

Each detection optical fiber 34 has a second diameter D2, with a value substantially constant from one fiber 34 to the next. The value of the second diameter D2 is preferably equal to 0.5 mm, and typically comprised between 10 μm and 1 mm, or even 5 mm. The value of the second diameter D2 is generally higher than that of the first diameter D1. This makes it possible to better collect fluorescence signals.

The protective housing 40 has, in a plane parallel to the X and Y axes, a third diameter D3 with a value preferably comprised between 1.5 mm and 3.5 mm, as shown in FIG. 3.

The focusing lens 42 has, in a plane parallel to the X and Y axes, a fourth diameter D4 with a value preferably comprised between 1 mm and 3 mm. The focusing lens 42 offers a wide viewing field, preferably comprised between 45° and 90°, and a large depth of field, preferably comprised between 1 mm and 40 mm.

The lens 42 is a fixed focus lens. Alternatively, the lens 42 is a variable focus lens, to automatically update or change the size of the covered field.

The optical filter 44 is a filter of the bandpass type, with a bandpass centered on the wavelength of interest.

The optical filter 44 is in the form of a film positioned between the lens 42 and the image sensor 18. In one alternative not shown, the optical filter 44 is made up of a thin layer deposited on the image sensor 18.

The memory 48 is capable of storing a first software application 52 for computing a parameter related to the time distribution obtained by each first detector 16 when the medium is excited by a pulsed source 14. Each time distribution is denoted $M_{sd}(t)$, the index sd designating the considered source—first detector pair. The first software application then establishes a characteristic magnitude of that time distribution $M_{sd}(t)$. That magnitude is in particular obtained by a transform of the considered time distribution $M_{sd}(t)$. The transform is for example a Mellin transform, making it possible to determine the moment of order 0, denoted $M^{(0)}_{sd}$, of the time distribution $M_{sd}(t)$ for each source 14—first detector 16 pair. Such a transform also makes it possible to determine a moment of order 1 denoted $M^{(1)}_{sd}$, of the time distribution ($M_{sd}(t)$) for each source 14—first detector 16 pair.

The moment of order 0 $M^{(0)}_{sd}$ of a time distribution corresponds to the intensity $I_{sd}$ of the signal emitted by the medium, i.e. the quantity of photons detected. As previously mentioned, the second detector 22 is not time-resolved, and it is therefore not able to determine the time distribution of the optical signal detected in response to a pulse from the excitation source 14. However, the second detector 22 directly measures an intensity $I_{sd'}$ of the optical signal emitted by the medium in response to excitation. Such an intensity $I_{sd'}$ can be likened to a moment of order $M^{(0)}_{sd'}$ of the optical signal emitted by the medium in response to the excitation by the source 14. In other words, the measurement $I_{sd'}$ of the second detector is equivalent to a moment of order 0. In other words, the measurement $I_{sd'}$ done by the second detector corresponds to an equivalent moment of order 0 $M^{(0)}_{sd'}$ for the source 14—second detector 22 pair associated with the index sd'.

The moments $M^{(0)}_{sd}$, $M^{(0)}_{sd'}$ of order 0 verify the following equations:

$$M^{(0)}_{sd} = \int_0^\infty M_{sd}(t) \cdot t^0 \, dt = I_{sd} \quad (1)$$

The moment $M^{(1)}_{sd}$ of order 1 verifies the following equation:

$$M^{(1)}_{sd} = \int_0^\infty M_{sd}(t) \cdot t^1 \, dt \quad (2)$$

In general, the moment $M^{(n)}_{sd}$ of order n verifies the following equation:

$$M^{(n)}_{sd} = \int_0^\infty M_{sd}(t) \cdot t^n \, dt \quad (3)$$

Alternatively, the first computation means 52 are made in the form of programmable logic components or in the form of dedicated integrated circuits.

The information processing unit 24 includes a device 56 for determining, as a function of the computed moments of order 0 and order 1 $M^{(0)}_{sd}$, $M^{(0)}_{sd'}$, $M^{(1)}_{sd}$, the location of N fluorophore(s) 28 in the medium 12, with $M^{(0)}_{sd'} = I_{sd'}$, each first detector 14 then being able to receive a fluorescence signal emitted by the fluorophore 28 and each second detector 22 being able to measure the intensity $I_{sd'}$ of the emitted fluorescence signal. N is an integer greater than or equal to 1.

The determination device 56 includes a software application 58 for producing a mesh of a volume of the medium 12, the mesh including M elementary link(s), M being an integer greater than or equal to 1, and a software application 60 for distributing the N fluorophore(s) 28 in the medium 12, each fluorophore 28 being distributed in one of the M mesh(es) of the medium according to a configuration m.

The determination device 56 includes a second software application 62 for computing at least one base parameter $X^N_{j,m}$, the or each base parameter combining, for at least one time distribution $M_{sd}(t)$ detected by a first detector 16, at least one magnitude obtained from at least one moment of said distribution and at least one estimate of that magnitude, j representing an index of the computed base parameter. Likewise, the base parameter $X^N_{j,m}$ combines a magnitude $M^{(0)}_{sd'}$ coming from the first signal measured by a second detector 22 and an estimate $M^{theo0}_{sd'}$ of said magnitude.

The software for producing a mesh 58, the software for distributing the fluorophore 60, and the second computation software application 62 can be stored in the memory 48.

The production of the mesh, the distribution of the fluorophores 28 and the computation of the base parameters are explained in document EP 2 302 362 A1 published on Mar. 30, 2011, in particular in the passages from page 6, line 25 to page 11, line 45 and from page 14, line 24 to page 25, line 6, in light of the figures associated with those passages, with the base parameters $X^N_{1,m}$, $X^N_{2,m}$, $X^N_{4,m}$, verifying the following equations for the present invention:

$$\chi^N_{1,m} = \min_{\alpha_1, \alpha_2, \ldots, \alpha_N} \left[ \sum_{sd} \frac{(M^{(0)}_{sd} - M^{theo0}_{sd,m}(\alpha_1, \alpha_2, \ldots, \alpha_N))^2}{\sigma^2(M^{(0)}_{sd})} + \sum_{sd'} \frac{(M^{(0)}_{sd'} - M^{theo0}_{sd',m}(\alpha_1, \alpha_2, \ldots, \alpha_N))^2}{\sigma^2(M^{(0)}_{sd'})} \right] \quad (4)$$

-continued $$\chi_{2,m}^N = \min_{\alpha_1, \alpha_2, \ldots, \alpha_N} \sum_{sd} \frac{((T_{sd} - T_s - \tau - T_d) - (T_{sd,m}^{theo0}(\alpha_1, \alpha_2, \ldots, \alpha_N)))^2}{\sigma^2(T_{sd})} \quad (5)$$

$$\chi_{4,m}^N = \min_{\alpha_1, \alpha_2, \ldots, \alpha_N} \left[ \begin{array}{l} \sum_{sd} \frac{(M_{sd}^{(0)} - M_{sd,m}^{theo0}(\alpha_1, \alpha_2, \ldots, \alpha_N))^2}{\sigma^2(M_{sd}^{(0)})} + \\ \sum_{sd'} \frac{(M_{sd'}^{(0)} - M_{sd',m}^{theo0}(\alpha_1, \alpha_2, \ldots, \alpha_N))^2}{\sigma^2(M_{sd'}^{(0)})} + \\ \sum_{sd} \frac{((T_{sd} - T_s - \tau - T_d) - (T_{sd,m}^{theo0}(\alpha_1, \alpha_2, \ldots, \alpha_N)))^2}{\sigma^2(T_{sd})} \end{array} \right] \quad (6)$$

where $T_{sd}$ represents the time of flight between the source 14 and the first detector 16, $T_s$ represents the average response time of the source 14, τ represents the fluorescence duration of the fluorophore 28, $T_d$ represents the average response time of the first detector 16, σ(X) represents a statistical magnitude relative to the estimate of the magnitude X. This normalization time is optional. It in particular translates the precision of this estimate. This is, for example, a standard deviation or a variance.

$\alpha_1, \alpha_2, \ldots, \alpha_N$ are coefficients each allocated to a corresponding fluorophore 28 and representing the emission intensity of the fluorescence by the latter. These coefficients are obtained during the minimization operation corresponding to equations (4), (5) or (6).

The time of flight $T_{sd}$ verifies the following equation:

$$T_{sd} = \frac{\int_0^\infty M_{sd}(t) \cdot t^1 \cdot dt}{\int_0^\infty M_{sd}(t) \cdot t^0 \cdot dt} \quad (7)$$
$$= M_{sd}^{(0)} / M_{sd}^{(1)}$$

In other words, the terms of the base parameters $X_{1,m}^N$ and $X_{4,m}^N$ including moments of order 0 are calculated with the moments $M_{sd}^{(0)}$, $M_{sd'}^{(0)}$ for the first and second detectors 16, 22, while the terms of the base parameters $X_{2,m}^N$ and $X_{4,m}^N$ including moments of order 1 are computed with the moments $M_{sd}^{(1)}$ for the first detector 16 only.

Thus, in general, a magnitude that is characteristic of the time distribution $M_{sd}(t)$ corresponding to at least one source 14—first detector pair (index sd) is combined with the intensity $I_{sd'}$ measured for at least one source 14—second detector 22 pair (index sd'). The combination thus gives rise to a base parameter $X_{1,m}^N$, $X_{2,m}^N$, $X_{4,m}^N$, from which the fluorescence is reconstructed.

It is useful to use the moment of order 1 associated with a source—first detector 16 pair. In fact, the inventors have shown that using such a moment makes it possible to obtain the time of flight $T_{sd}$, that magnitude being particularly representative of the depth of the fluorophore the medium. Furthermore, the moment of order 0 is more sensitive to the position of the fluorophore in a plane parallel to the surface of the medium, i.e. in the plane of axes X and Y in the example embodiment of FIG. 1.

It will be understood that by using base parameters $X_{1,m}^N$, $X_{2,m}^N$, $X_{4,m}^N$, combining moments of order 1 and moments of order 0, one obtains precise information on the position of the detector in the plane of axes X and Y, as well as the depth along the Z axis.

As previously mentioned, the time distribution $M_{sd}(t)$ associated with a source-detector pair can fluctuate due to the instability of the first time-resolved detector 16. It will then be understood that the base parameters defined above are more robust inasmuch as they are prepared from equivalent intensities $I_{sd'}(t)$ at moments of order 0 $M_{sd'}^{(0)}$, measured on detectors where the response is stable, i.e. detectors 22 of the second type, non-time-resolved.

One advantage of the invention is then to combine:

measurements from at least one first time-resolved detector 16, as they make it possible to determine the time of flight $T_{sd}$, and, starting from there, information on the depth of the fluorophore, intensities $I_{sd'}$ measured by at least one second non-time-resolved detector 22, the latter being more stable, and bearing information on the position of the fluorophore in a plane of axes X and Y, perpendicular to the Z-axis defining the depth.

It will also be noted that when the terms $$\sum_{sd} \frac{(M_{sd}^{(0)} - M_{sd,m}^{theo0}(\alpha_1, \alpha_2, \ldots, \alpha_N))^2}{\sigma^2(M_{sd}^{(0)})}$$

and $$\sum_{sd'} \frac{(M_{sd'}^{(0)} - M_{sd',m}^{theo0}(\alpha_1, \alpha_2, \ldots, \alpha_N))^2}{\sigma^2(M_{sd'}^{(0)})}$$

are combined, the normalization coefficient $\sigma^2(M_{sd}^{(0)})$ will for example be lower than the normalization coefficient $\sigma^2(M_{sd'}^{(0)})$. This makes it possible to weight the effective measurements obtained using unstable detectors, to the benefit of measurements obtained using stable detectors. It will be recalled that the use of such normalization coefficients is optional.

Alternatively, the means for producing a mesh 58, the means for distributing the fluorophores 60, and the second computation means 62 are made in the form of programmable logic components in the form of dedicated integrated circuits.

The operation of the reconstruction system 10 according to the invention is described below using FIG. 3, showing a flowchart of the reconstruction method according to the invention.

Before its use, the system 10 is calibrated, during step 100, using a phantom having known optical characteristics. The phantom is a phantom having absorption $\mu_a$ and diffusion $\mu_s'$ coefficients with median values for human tissues, for example equal to 0.2 cm$^{-1}$ and 10 cm$^{-1}$, respectively. This preliminary calibration 100 makes it possible to verify the operation of the system 10, and to parameterize it as a function of any detected biases. These potential biases are for example due to a variation in the power of the sources 14, the presence of dust on the lens 42, and/or the modification of the coupling efficiency of the optical fibers 32, 34 due to temperature variations.

An area of the medium 12 to be analyzed is then identified, during step 110, using the image sensor 18. The tissues of the medium are lit by each pulsed light source 30 with a frequency such that the image sensor 18 perceives it as a continuous light. This frequency is preferably comprised between 10 and 100 MHz. The exposure time of the image sensor 18, comprised between 1 ms and 100 ms, then does not make it possible to distinguish the light pulses, and the image displayed on the monitor 25 using the sensor 18 does not show any blinking.

After identifying the area to be analyzed, that area is lit by each pulsed radiation source 14 (step 120), and pulsed light is then backscattered by the tissues of the medium 12. This backscattered light is collected by the second detectors 22 of the image sensor, as well as by the first detector 16, the detection fibers 34 of which are placed on the image sensor 18.

The second detectors 22 make it possible to measure the equivalent moment of order 0 $M^{(0)}_{sd'}$ directly, without processing a time distribution for the second detectors 22. The detection optical fibers 34 lead the light to the time-resolved detection module 36, and the processing means 50, connected to the time-resolved detection module 36, then make it possible to process the time distribution $M_{sd}(t)$ of the arrival times of photons in each detection fiber 34 (step 130).

The system 10 therefore has two types of measurement, i.e. intensity measurements $I_{sd'}$ at a large number of points, directly provided by the image sensor 18, and measurements of the time distribution $M_{sd}(t)$ of the photons picked up by the detection fibers 34, using the time-resolved detection module 36 connected to those detection fibers 34. This makes it possible to determine a map of the optical properties (step 140) and/or to locate the N fluorophore(s) 28 in the area to be analyzed (step 150).

During step 140, the reconstruction aims to determine the spatial distribution of the optical absorption $\mu_a$ and diffusion D properties of the diffusing medium 12.

To that end, the Mellin-Laplace transform is for example used for the distribution $M_{sd}(t)$ measured by a first detector 16.

The Mellin-Laplace transform of order n and width p of a function f is denoted $f^{(p,n)}$, and verifies the following equation:

$$f^{(p,n)} = \frac{1}{n!} \int_0^{+\infty} (pt)^n \cdot \exp(-pt) \cdot f(t) \cdot dt \tag{8}$$

where 1/n! represents an optional normalization term.

The Mellin-Laplace transform $f^{(p,n)}$ of the function f is also written:

$$f^{(p,n)} = \int_{-\infty}^{+\infty} W^{(p,n)} \cdot f(t) \cdot dt \tag{9}$$

where $W^{(p,n)}$ represents a time window defined by the following equation:

$$W^{(p,n)} = \frac{H(t) \cdot (pt)^n \cdot \exp(-pt)}{n!} \tag{10}$$

with H(t) representing the known Heaviside function.

The reconstruction is done using an iterative method, by performing a distribution $M_{sd}(t)$ for one or more source-detector pair(s).

This time distribution $M_{sd}(t)$ verifies the following equation:

$$M_{sd}(t) = IRF_{sd}(t) * G_{sd}(t) \tag{11}$$

where $IRF_{sd}(t)$ represents the instrument response, i.e. the influence of the source s and the detector d on the first processed distribution,

* designates the convolution integral, and $G_{sd}(t)$ represents a first modeling function for a diffusion signal of the light between the source 14 and the first detector 16 in the diffusing medium 12.

$S_s(t)$ denotes the time response of the source 14, also denoted s. The source 14 is a brief light pulse, often modeled using a distribution of the periodic Dirac type. $S_s(t)$ represents the time intensity of the emitted signal.

$D_d(t)$ denotes the time response of the first detector 16, also denoted d. This response in particular translates the time-frame between the arrival of a photon on the detector 16 and its actual detection.

The instrument response, denoted $IRF_{sd}(t)$, the index sd corresponding to an excitation source 14—first detector 16 pair, is generally estimated. This instrument response is obtained by combining $S_s(t)$ and $D_d(t)$ as follows: $IRF_{sd}(t) = S_s(t) * D_d(t)$, where * designates the convolution integer.

When there are several sources and several detectors, $IRF_{sd}(t)$ is determined for each source-detector pair, since each source and each detector has its own response. In practice, this is done by placing a source (or an optical fiber then constituting the source) across from a first detector (or an optical fiber then constituting the detector). This assumes careful alignment between the source and the first detector, and takes time, in particular when the number of sources and detectors increases. For example, 100 instrument response functions $IRF_{sd}$ must be determined when there are 10 sources and 10 detectors.

For each source-detector pair, the following equation is then obtained:

$$M_{sd}(t) - M_{sd}^1(t) = -S_s(t) * (\int G_s^1(\vec{r},t) * \delta\mu_a(\vec{r},t) * G_d^1(\vec{r},t) \, d\vec{r} + \int \vec{\nabla} G_s^1(\vec{r},t) * \delta D(\vec{r},t) * \vec{\nabla} G_d^1(\vec{r},t) d\vec{r}) * D_d(t) \tag{12}$$

where:

$M_{sd}^1$ represents a modeled measurement considering that the medium has the absorption $\mu_a^1(r)$ and diffusion $D_a^1(r)$ coefficients determined during the previous iteration, the values $\mu_a^1(r)$ and $D_a^1(r)$ being initialized during the first iteration by a first estimate done by the operator, $G_s(r,t) = G(r_s,r,t)$ is the Green function representing the density of photons at a location r of the medium 12 when the medium is lit by the source s situated at $r_s$, $G_d(r,t) = G(r_d,r,t)$ is the Green function representing the density of photons at the location r of the medium 12 when the medium is lit by the source s situated at $r_d$. It is also written $G_d(r,t) = G(r,r_d,t)$. Thus, this Green function also represents the density of photons at the detector ($r_d$) when the medium 12 is lit by a source situated at r.

the coefficients $\delta\mu_a(\vec{r},t)$ and $\delta D(\vec{r},t)$ represent the difference between the optical properties of the medium ($\mu_a$, D) and the initial optical properties ($\mu_a^1$, $D^1$), or those resulting from the previous iteration.

The goal is to minimize $\delta\mu_a(\vec{r},t)$ and $\delta D(\vec{r},t)$.

The Mellin Laplace transforms of a function $Y_{sd}$ are determined, those transforms assuming the form:

$$Y_{s,d}^{(p,n)} = \frac{M_{s,d}^{(p,n)} - \sum_{i=0}^{n-1} IRF_{s,d}^{(p,n-i)} M_{s,d}^{(p,i)}}{I_{s,d}^{(p,0)}} \tag{13}$$

Thus, as a function of the Mellin-Laplace transforms of the instrument response $IRF_{s,d}^{(p,k)}$, with $0 \leq k \leq n$, and the measurement $M_{s,d}^{(p,k)}$ with $0 \leq k \leq n$, one determines $Y_{s,d}^{(p,n)}$:

$$Y_{s,d}^{(p,n)} = \left( \int_\Omega \sum_{j+k=n} G_s^{1(p,j)}(\vec{r}) \cdot \delta\mu_a(\vec{r}) \cdot G_d^{1(p,k)}(\vec{r}) d\vec{r} + \int_\Omega \sum_{j+k=n} G_s^{1(p,j)}(\vec{r}) \cdot \delta D(\vec{r}) \cdot G_d^{1(p,k)}(\vec{r}) d\vec{r} \right) \quad (14)$$

After discretization of the medium in M voxels m, this expression becomes:

$$Y_{s,d}^{(p,n)} = \sum_{m=1}^{M} \left( \sum_{j+k=n} G_s^{1(p,j)}(\vec{r}_m) \cdot \delta\mu_a(\vec{r}_m) \cdot G_d^{1(p,k)}(\vec{r}_m) V_m + \sum_{j+k=n} G_s^{1(p,j)}(\vec{r}_m) \cdot \delta D(\vec{r}_m) \cdot G_d^{1(p,k)}(\vec{r}_m) V_m \right) \quad (15)$$

The reconstruction step then aims to resolve the following matrix system:

$$\underline{Y} = \underline{W}\underline{X}, \quad (16)$$

where $\underline{Y}$ represents a vector of the observations, $\underline{W}$ represents a transition matrix, and $\underline{X}$ represents a vector of the unknowns.

The vector of the observations $\underline{Y}$ contains the Nn Mellin-Laplace transforms of the function $Y_{s,d}^{(p,n)}$, with Nn equal to $n_{max}+1$, calculated for all of the successive values of the order n comprised between 0 and $n_{max}$ and for the considered source-detector pairs (s, d).

One defines, for each triplet (s, d, n) of the indices s, d and the order n, an index i.e. as follows:

$$I = (s-1) \times Nd \times Nn + (d-1) \times Nn + n \quad (17)$$

where Nd is the considered number of detectors 16.

The maximum value of the index I is equal to Imax, such that:

$$I_{max} = Ns \times Nd \times Nn \quad (18)$$

The vector of the observations $\underline{Y}$ then includes Imax lines.

The transition matrix $\underline{W}$ comprises a first portion $W^\mu$ including first terms denoted $W^\mu(I,m)$ and a second portion $W^D$ including second terms denoted $W^D(I,m)$. This matrix is called the sensitivity matrix of the measurements Y to the optical properties X.

The transition matrix $\underline{W}$ then includes Imax lines and 2M columns.

Each term $W^\mu(I,m)$, $W^D(I,m)$ of the transition matrix $\underline{W}$ is determined by modeling upon each iteration, as a function of the optical properties determined during the previous iteration or during the first iteration, as a function of the optical properties initialized by the operator. This initialization is done for example considering a homogenous medium 12.

The vector of the unknowns $\underline{X}$ includes 2M lines and one column, and contains the unknowns $\mu_a(m)$ and $D(m)$ for each of the M voxels. The first M lines correspond to the unknowns $\mu_a(m)$ and the following M lines of the vector $\underline{X}$ correspond to the unknowns $D(m)$.

The inversion of the transition matrix $\underline{W}$ is done using inversion algorithms well known by those skilled in the art, such as a gradient descent algorithm, an algebraic reconstruction technique (ART), a singular value decomposition (SVD), or a conjugated gradients method. The process stops when a convergence criterion is achieved, for example when the distance between two successive factors $\underline{X}$ is below a predetermined threshold.

During the reconstruction described above, each distribution $M_{sd}(t)$ can be affected by the instability of a first time-resolved detector 16.

A second detector 22 is then selected, where one measures the intensity $I_{sd'}$, and that more stable measurement is used to correct the time distribution $M_{sd}(t)$. Preferably, the second detector 22 is placed near the first considered detector 16.

One example of correction is provided by the following equation, $M*sd(t)$ representing the corrected distribution Msd(t), the Mellin Laplace transforms of which are determined and used for the reconstruction according to the previously described principles.

$$M*_{sd}(t) = M_{sd}(t) * \frac{I_{sd'}}{M_{sd}^0} \quad (19)$$

Thus, the combination of measurements from a first time-resolved detector 16 and a second non-time-resolved detector 22 makes it possible to attenuate the previously described instability effects. It will be understood that the correction term $$\frac{I_{sd'}}{M_{sd}^0}$$

is particularly appropriate when a series of measurements is done using the same source—first detector pair sd and the same source—second detector pair sd'.

This type of correction is not limited to this embodiment, and can be considered when one wishes to reconstruct the fluorescence properties of the examined medium (step 150).

During step 150, the reconstruction aims to determine the fluorescence properties of the diffusing medium, the N fluorophore(s) 28 are localized using the determination device 56 by computing the base parameters $X^N_{1,m}, X^N_{2,m}, X^N_{4,m}, X^N_{5,m}$ using equations (4) to (6), considering that the values of the base parameters $X^N_{1,m}, X^N_{2,m}, X^N_{4,m}, X^N_{5,m}$ are minimal for the configurations m closest to the actual configuration of the N fluorophore(s) 28 in the medium 12. The base parameter $X^N_{1,m}$ is the parameter preferably chosen from among the base parameters $X^N_{1,m}, X^N_{2,m}, X^N_{4,m}, X^N_{5,m}$ to localize the N fluorophore(s) 28.

The reconstruction system 10 according to the invention therefore calculates the moments of order 0 using two types of measurements, i.e. intensity measurements $I_{sd'}$ at a large number of points, these being directly provided by the second detectors 22 of the image sensor 18, and measurements of the time distribution $M_{sd}(t)$ of the photons picked up by the detection sensors 34 of the first detector 16. This makes it possible to reduce the parasitic fluctuations in terms of base parameters $X^N_{1,m}$ and $X^N_{4,m}$ having moments of order 0, whereas in the reconstruction system of the state of the art, the moments of order 0 of the terms of the base parameters $X^N_{1,m}$ and $X^N_{4,m}$ are calculated exclusively for the time distribution $M_{sd}(t)$ of the photons picked up by the time-resolved detectors. The fluorophores are thus better localized.

Alternatively, the reconstruction system 10 calculates the moments of order 0 using only the intensity measurements $I_{sd'}$ directly provided by the second detectors 22 of the image sensor 18.

In other words, only the moment of order 1 $M^{(1)}_{sd}$ of the time distribution $M_{sd}(t)$ is calculated for each source 14—first detector 16 pair.

According to this alternative, the base parameters $X_{1,m}$, $X^N_{2,m}$, $X^N_{4,m}$ verify the following equations:

$$\chi^N_{1,m} = \min_{\alpha_1, \alpha_2, \ldots, \alpha_N} \left[ \sum_{sd'} \frac{(M^{(0)}_{sd'} - M^{theo0}_{sd',m}(\alpha_1, \alpha_2, \ldots, \alpha_N))^2}{\sigma^2(M^{(0)}_{sd'})} \right] \quad (20)$$

$$\chi^N_{2,m} = \min_{\alpha'_1, \alpha'_2, \ldots, \alpha'_N} \sum_{sd} \frac{((T_{sd} - T_s - \tau - T_d) - (T^{theo0}_{sd,m}(\alpha_1, \alpha_2, \ldots, \alpha_N)))^2}{\sigma^2(T_{sd})} \quad (21)$$

$$\chi^N_{4,m} = \min_{\alpha_1, \alpha_2, \ldots, \alpha_N} \left[ \sum_{sd'} \frac{(M^{(0)}_{sd'} - M^{theo0}_{sd',m}(\alpha_1, \alpha_2, \ldots, \alpha_N))^2}{\sigma^2(M^{(0)}_{sd'})} + \sum_{sd} \frac{((T_{sd} - T_s - \tau - T_d) - (T^{theo0}_{sd,m}(\alpha_1, \alpha_2, \ldots, \alpha_N)))^2}{\sigma^2(T_{sd})} \right] \quad (22)$$

The terms of the base parameters $X^N_{1,m}$ and $X^N_{4,m}$ include moments of order 0 then no longer depending on the parasitic variations of the moments of order 0 calculated using the first detectors 16. The fluorophores are also better localized.

According to another embodiment, not shown, the second detectors 22 are not situated near the excitation optical fibers 32 and first detector 16, but rather are separated from the latter by the examined diffusing medium.

In other words, the first detector 16 operates according to a backscattering mode, while the second detectors 22 operate according to a transmission mode. This configuration is in particular suitable for applications of the mammography type, the breast to be analyzed then being positioned between the source 14 (or the end of the excitation fibers) and the second detectors 22. Preferably, the first time-resolved detectors 16 operate in a backscattering mode, i.e. they measure an optical signal backscattered by the medium, the medium not being inserted between the excitation source 14 and said first detectors 16.

In this way, the first and second detectors 16, 22 operate in a backscattering mode, or according to a transmission mode, the idea of the invention being to combine their respective signals so as to reconstruct the optical properties of the examined diffusing medium.

One can see that the reconstruction system 10 according to the invention makes it possible to reduce the influence of parasitic fluctuations of the time distributions obtained by the time-resolved optical detectors, so as to improve the reconstruction of the optical properties.

The invention claimed is:

1. A system for reconstructing optical properties of a diffusing medium, the reconstruction system comprising:
    at least one pulsed radiation source capable of illuminating the diffusing medium,
    at least one first detector of a first type, capable of receiving a signal emitted by the medium, the at least one first detector being a time-resolved detector,
    a processing unit connected to the at least one first detector, for at least one source—first detector pair, the processing unit producing a time distribution of the signal received by the corresponding first detector,
    at least one second detector of a second type distinct from the first type, the at least one second detector being made up of a set of pixel(s) from an image sensor capable of acquiring an image of the medium, the at least one second detector being capable of measuring an intensity of the signal emitted by the medium, said intensity corresponding to an equivalent moment of order 0 for the corresponding source—second detector pair, and
    said processing unit computing at least one base parameter by combining a magnitude that is characteristic of the time distribution corresponding to at least one source—first detector pair with the intensity measured for at least one source—second detector pair, the optical properties being reconstructed from the computed base parameter.

2. The system according to claim 1, wherein the at least one second detector is a non-time-resolved detector.

3. The system according to claim 1, wherein the processing unit computes the moment of order 0 of the time distribution for each source—first detector pair and the equivalent moment of order 0 for each source—second detector pair.

4. The system according to claim 1, wherein the processing unit computes a single moment of order 1 of the time distribution for each source—first distribution pair.

5. The system according to claim 4, wherein the system comprises a device for determining, as a function of the computed moments of order 0 and order 1, the localization of N fluorophore(s) in the medium, N being an integer greater than or equal to 1, each first detector being capable of receiving a fluorescence signal emitted by the fluorophore and each second detector being capable of measuring the intensity of the emitted fluorescence signal.

6. The system according to claim 5, wherein the determination device produces a mesh of a volume of the medium, the mesh including M elementary link(s), M being an integer greater than or equal to 1, and distributes N fluorophore(s) in the medium, each fluorophore being distributed in one of the M link(s) of the medium according to a configuration, and the processing unit computes at least one base parameter, the at least one base parameter combining, for at least one time distribution, at least one magnitude obtained from at least one moment of said distribution and at least one estimate of that magnitude.

7. The system according to claim 1, wherein the system also comprises a lens for focusing the signals emitted by the medium, each second detector being positioned in the image plane of the lens.

8. The system according to claim 1, wherein the system also comprises an optical filter arranged between the medium and the image sensor, so as to filter the signals emitted by the medium to the image sensor.

9. The system according to claim 1, wherein each first detector includes an optical fiber coupled to a time-resolved detection module.

10. The system according to claim 1, wherein the image sensor is a CCD sensor or a CMOS sensor.

11. The system according to claim 1, wherein the optical properties comprise at least one element from among the following group:
    light absorption properties, characterized in particular by the absorption coefficient,
    diffusion properties, characterized in particular by the reduced diffusion coefficient or the diffusion coefficient, and
    fluorescence properties, in particular characterized by a response function of a fluorophore, or by a concentration of the fluorophore, or by a magnitude depending on a quantity of the fluorophore.

12. A method for reconstructing optical properties of a diffusing medium, using a reconstruction system including at least one pulsed radiation source, at least one first detector of a first type, the at least one first detector being a time-resolved detector, the method comprising the following steps:

lighting the medium using each pulsed radiation source, reception, by the at least one first detector, of a signal emitted by the medium, and processing, for at least one source—first detector pair, a time distribution of the signal received by the corresponding first detector, measuring the intensity of the signal emitted by the medium by acquiring an image of the medium using at least one second detector of a second type distinct from the first type, said intensity corresponding to an equivalent moment of order 0 for the corresponding source—second detector pair, the at least one second detector being included in the reconstruction system and made up of a set of pixel(s) from an image sensor; and computing at least one base parameter by combining a magnitude that is characteristic of the time distribution corresponding to the at least one source—first detector pair with the intensity measured for at least one source—second detector pair, the optical properties being reconstructed from the computed base parameter.

13. The method according to claim 12, wherein the method also comprises computing the moment of order 0 of the time distribution for each source—first detector pair and the equivalent moment of order 0 for each source—second detector pair.

14. A system for reconstructing optical properties of a diffusing medium, the reconstruction system comprising:

at least one pulsed radiation source capable of illuminating the diffusing medium, at least one first detector of a first type, capable of receiving a signal emitted by the medium, the at least one first detector being a time-resolved detector, a processing unit connected to the at least one first detector, for at least one source—first detector pair, the processing unit producing a time distribution of the signal received by the corresponding first detector, at least one second detector of a second type distinct from the first type, the at least one second detector being made up of a set of pixel(s) from an image sensor capable of acquiring an image of the medium, the at least one second detector being capable of measuring an intensity of the signal emitted by the medium, said intensity corresponding to an equivalent moment of order 0 for the corresponding source—second detector pair, said processing unit computing at least one base parameter by combining a magnitude that is characteristic of the time distribution corresponding to at least one source—first detector pair with the intensity measured for at least one source—second detector pair, the optical properties being reconstructed from the computed base parameter, and said processing unit computing a correction factor associated with the time distribution of the at least one source—first detector pair, the correction factor depending on the intensity measured by a second corresponding detector and the moment of order 0 computed for said at least one source—first detector pair.

15. A method for reconstructing optical properties of a diffusing medium, using a reconstruction system including at least one pulsed radiation source, at least one first detector of a first type, the at least one first detector being a time-resolved detector, the method comprising the following steps:

lighting the medium using the or each pulsed radiation source, reception, by the at least one first detector, of a signal emitted by the medium, and processing, for at least one source—first detector pair, a time distribution of the signal received by the corresponding first detector, measuring the intensity of the signal emitted by the medium by acquiring an image of the medium using at least one second detector of a second type distinct from the first type, said intensity corresponding to an equivalent moment of order 0 for the corresponding source—second detector pair, the at least one second detector being included in the reconstruction system and made up of a set of pixel(s) from an image sensor;

computing at least one base parameter by combining a magnitude that is characteristic of the time distribution corresponding to the at least one source—first detector pair with the intensity measured for at least one source—second detector pair, the optical properties being reconstructed from the computed base parameter; and computing a correction factor associated with the time distribution of at least one source—first detector pair, the correction factor depending on the intensity measured by a second corresponding detector and the moment of order 0 computed for said at least one source—first detector pair.

* * * * *